(12) United States Patent
Savall et al.

(10) Patent No.: US 11,980,435 B2
(45) Date of Patent: May 14, 2024

(54) USER INTERFACE DEVICE HAVING GRIP LINKAGES

(71) Applicant: Verb Surgical Inc., Santa Clara, CA (US)

(72) Inventors: Joan Savall, Palo Alto, CA (US); Allegra Anna Lenta Shum, San Francisco, CA (US)

(73) Assignee: Verb Surgical Inc., Santa Clara, CA (US)

( * ) Notice: Subject to any disclaimer, the term of this patent is extended or adjusted under 35 U.S.C. 154(b) by 141 days.

(21) Appl. No.: 17/488,209

(22) Filed: Sep. 28, 2021

(65) Prior Publication Data
US 2022/0015852 A1    Jan. 20, 2022

Related U.S. Application Data

(63) Continuation of application No. 16/010,054, filed on Jun. 15, 2018, now Pat. No. 11,135,031.

(51) Int. Cl.
*A61B 34/00* (2016.01)
*A61B 17/00* (2006.01)
(Continued)

(52) U.S. Cl.
CPC .............. *A61B 34/74* (2016.02); *A61B 17/29* (2013.01); *A61B 34/20* (2016.02); *A61B 34/35* (2016.02);
(Continued)

(58) Field of Classification Search
CPC . A63F 13/212; A61B 34/30; A61B 2034/305; A61B 34/74; A61B 34/75;
(Continued)

(56) References Cited

U.S. PATENT DOCUMENTS

| 5,441,494 A | 8/1995 | Ortiz |
| 6,587,750 B2 | 7/2003 | Gerbi et al. |
| (Continued) | | |

FOREIGN PATENT DOCUMENTS

| CN | 106999186 A | 8/2017 |
| CN | 107847284 A | 3/2018 |
| (Continued) | | |

OTHER PUBLICATIONS

First Office Action dated Mar. 2, 2022 from related Chinese Patent Application No. 201811433060.7, 22 pages including translation.
(Continued)

*Primary Examiner* — Kankindi Rwego
(74) *Attorney, Agent, or Firm* — Aikin & Gallant, LLP

(57) ABSTRACT

User interface devices for manipulating a robotic surgical tool in a surgical robotic system are described. A user interface device can include a device body containing a tracking sensor to generate a spatial state signal in response to movement of the device body. The spatial state signal can be used to control a spatial motion of a surgical robotic system actuator. Several grip linkages can be pivotally coupled to the device body. A grip linkage displacement sensor may monitor movement of the grip linkages relative to the device body, and generate a grip signal in response to the movement. The grip signal can be used to control a grip motion of a robotic surgical tool mounted on the surgical robotic system actuator. Other embodiments are also described and claimed.

20 Claims, 9 Drawing Sheets

(51) Int. Cl.
    *A61B 17/29* (2006.01)
    *A61B 34/20* (2016.01)
    *A61B 34/35* (2016.01)

(52) U.S. Cl.
    CPC ............... *A61B 2017/00039* (2013.01); *A61B 2017/00075* (2013.01); *A61B 2017/00199* (2013.01); *A61B 2017/00212* (2013.01); *A61B 2017/00221* (2013.01); *A61B 2017/00398* (2013.01); *A61B 2017/2908* (2013.01); *A61B 2034/2048* (2016.02); *A61B 2034/2051* (2016.02); *A61B 2034/2061* (2016.02); *A61B 2034/742* (2016.02); *A61B 2034/743* (2016.02)

(58) Field of Classification Search
    CPC ... A61B 34/76; A61B 34/77; A61B 2034/741; A61B 2034/742; A61B 2034/743; A61B 2034/744; A61B 17/28; A61B 17/29
    USPC .......................................................... 606/130
    See application file for complete search history.

(56) References Cited

U.S. PATENT DOCUMENTS

| | | |
|---|---|---|
| 6,659,939 B2 | 12/2003 | Moll et al. |
| 6,995,744 B1 | 2/2006 | Moore et al. |
| 7,206,627 B2 | 4/2007 | Abovitz et al. |
| 7,865,266 B2 | 1/2011 | Moll et al. |
| 8,332,072 B1 | 12/2012 | Schaible et al. |
| 8,391,954 B2 | 3/2013 | Quaid, III |
| 8,521,331 B2 | 8/2013 | Itkowitz |
| 8,682,489 B2 | 3/2014 | Itkowitz |
| 8,831,782 B2 | 9/2014 | Itkowitz |
| 8,930,027 B2 | 1/2015 | Schaible et al. |
| 9,002,517 B2 | 4/2015 | Bosscher et al. |
| 9,108,318 B2 | 8/2015 | Diolaiti |
| 9,241,768 B2 | 1/2016 | Sandhu et al. |
| 10,117,649 B2 | 11/2018 | Baxter, III et al. |
| 10,130,429 B1 | 11/2018 | Weir |
| 2008/0154246 A1 | 6/2008 | Nowlin et al. |
| 2010/0228264 A1 | 9/2010 | Robinson |
| 2010/0302140 A1 | 12/2010 | Araki et al. |
| 2011/0118748 A1 | 5/2011 | Itkowitz |
| 2011/0118752 A1 | 5/2011 | Itkowitz |
| 2013/0304044 A1 | 11/2013 | Scheller et al. |
| 2014/0018960 A1 | 1/2014 | Itkowitz |
| 2014/0148820 A1 | 5/2014 | Ogawa |
| 2014/0160015 A1 | 6/2014 | Ogawa |
| 2015/0305761 A1 | 10/2015 | Kang et al. |
| 2017/0095298 A1 | 4/2017 | Vakharia et al. |
| 2017/0095922 A1 | 4/2017 | Licht et al. |
| 2018/0078319 A1 | 3/2018 | Nobles et al. |
| 2018/0221045 A1 | 8/2018 | Zimmerman et al. |
| 2018/0235719 A1 | 8/2018 | Jarc |

FOREIGN PATENT DOCUMENTS

| | | |
|---|---|---|
| JP | 2013035117 A | 2/2013 |
| JP | 2017-119168 A | 7/2017 |
| JP | 2018513711 A | 5/2018 |
| KR | 20130015440 A | 2/2013 |
| WO | 2013018934 A1 | 2/2013 |
| WO | 2016/001544 A1 | 1/2016 |
| WO | 2016137527 A1 | 9/2016 |
| WO | 2016201544 A1 | 12/2016 |
| WO | 2018107062 A1 | 6/2018 |

OTHER PUBLICATIONS

Second Office Action dated Aug. 31, 2022 from related Chinese Patent Application No. 201811433060.7, 3 pages.
Notification of Reasons for Refusal dated Feb. 15, 2022 from related Japanese Patent Application No. 2020-568720, 16 pages including translation.
Examiner's Decision of Refusal dated Oct. 4, 2022 from related Japanese Patent Application No. 2020-568720, 6 pages including translation.
International Search Report and Written Opinion dated Mar. 20, 2019 from related PCT Application No. PCT/US2018/037941, 13 pages.
European Communication Pursuant to Rules 161(1) and 162 EPC from related EP Application No. 18742873.5 dated Dec. 17, 2020, 3 pages.
PCT International Preliminary Report on Patentability from related PCT Application No. PCT/US2018/037941 dated Dec. 24, 2020, 9 pages.
Office Action received for Japanese Patent Application No. 2023-015211, dated Oct. 3, 2023, 12 pages (6 pages of English Translation and 6 pages of Original Document).

USER INTERFACE DEVICE HAVING GRIP LINKAGES

This application is a continuation of co-pending U.S. patent application Ser. No. 16/010,054, filed on Jun. 15, 2018, which application is hereby incorporated herein by reference in its entirety.

BACKGROUND

Field

Embodiments related to robotic systems are disclosed. More particularly, embodiments related to surgical robotic systems and corresponding user interface devices are disclosed.

Background Information

Endoscopic surgery involves looking into a patient's body and performing surgery inside the body using endoscopes and other surgical tools. For example, laparoscopic surgery can use a laparascope to access and view an abdominal cavity. Endoscopic surgery can be performed using manual tools and/or a surgical robotic system having robotically-assisted tools.

A surgical robotic system may be remotely operated by a surgeon to control a robotically-assisted tool located at an operating table. The surgeon may use a computer console located in the operating room, or it may be located in a different city, to command a robot to manipulate the surgical tool mounted on the operating table. The robotically-controlled surgical tool can be a grasper mounted on a robotic arm. Accordingly, the surgical robotic system may be controlled by the remote surgeon to grasp tissue during a robotic surgery.

Control of the surgical robotic system may require control inputs from the surgeon. For example, the surgeon may hold in her hand a user input device such as a joystick or a computer mouse that she manipulates to generate the signals for the control commands that control motion of the surgical robotic system components, e.g., an actuator, a robotic arm, and/or a surgical tool of the robotic system.

SUMMARY

Existing user input devices include hand controllers used to command a surgical robotic system. The hand controllers may include a grip that the surgeon manipulates to remotely command motion of an actuator coupled to a surgical tool. Furthermore, the surgeon may manipulate handles of the grip to command jaws of the surgical tool. Existing hand controllers, however, do not allow for precise finger manipulation, such as rotation, rolling, or twisting of the grip. Existing hand controllers do not provide tactile feedback to the surgeon related to the gripping configuration of the jaws, e.g., whether the jaws are in a closed or open configuration. Furthermore, existing hand controllers are not capable of locking the jaws in place, and may require the surgeon to exert a constant gripping force on the grip handles. As a result, a dexterity and precision of movements commanded by existing hand controllers may be limited, and the existing hand controllers may cause user fatigue.

A user interface device for manipulating a robotic surgical tool in a surgical robotic system is provided, which can provide command signals used to control highly dexterous, precise movement of a robotic actuator and/or robotic surgical tool. In an embodiment, the user interface device includes several, e.g., at least three, grip linkages coupled to a device body. Each grip linkage can include a grip crank pivotally coupled to the device body, a slider that slides over the device body, and a follower arm pivotally coupled between the grip crank and the slider. Accordingly, the grip cranks can be squeezed between the fingers of a user to change a position of the slider on the device body. The position of the slider can be measured by a grip linkage displacement sensor to generate a grip signal for manipulating a grip motion of a robotic surgical tool of a surgical robotic system. The user interface device can also include a tracking sensor, e.g., a six-degree-of-freedom electromagnetic tracker (for example on its device body) that is used for generating a spatial state signal, e.g., an input pose signal, in response to movement of the device body. The spatial state signal can be used by one or more processors to control a spatial motion of an actuator or a robotic surgical tool of the surgical robotic system. Accordingly, the user interface device can be used to control highly dexterous, precise movement of the robotic actuator and/or robotic surgical tool.

In an embodiment, a user interface device having grip linkages includes a bistable latching mechanism. The bistable latching mechanism can hold the grip linkages in a closed position when the grip linkages are squeezed fully inward. Once the grip linkages are at the closed position, the grip linkages can be released from the closed position and extend outward to an open position by again squeezing the grip linkages inward. The bistable latching mechanism allows a user to maintain a grasper of the robotic surgical tool in a fully closed position without requiring the user to constantly squeeze the user interface device. Accordingly, the bistable latching mechanism incorporated in the user interface device reduces the likelihood that an operator will experience hand fatigue.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
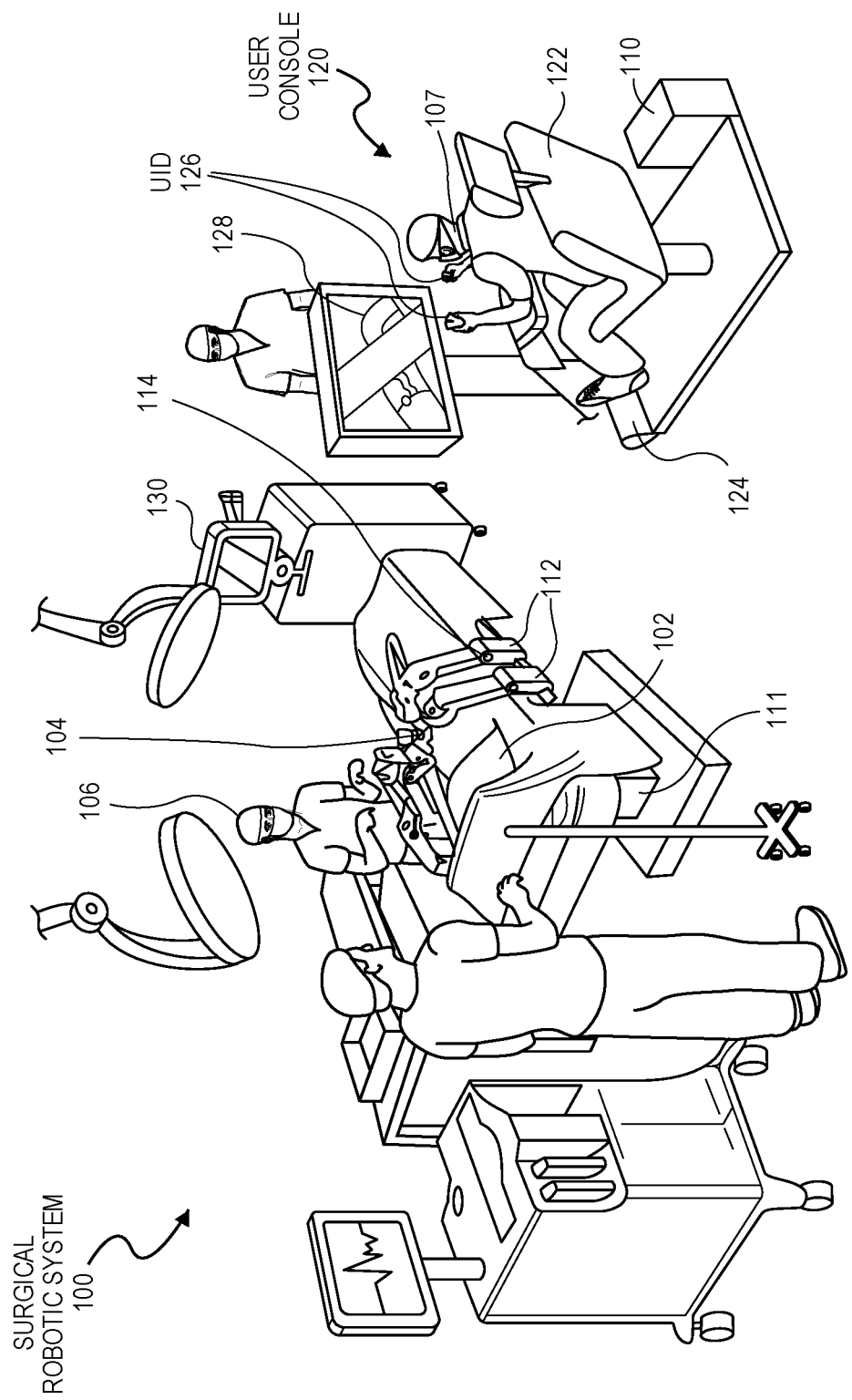
FIG. 1 is a pictorial view of an example surgical robotic system in an operating arena, in accordance with an embodiment.

Embodiments describe a user interface device (UID) for providing command signals used to control a robotic system. The robotic system can be a surgical robotic system. The UID signals may, however, be used to control other systems, such as interventional cardiology systems, vision systems, or aircraft systems, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of a UID to a specific configuration described in the various embodiments below.

In an aspect, a UID for manipulating a robotic surgical tool in a surgical robotic system includes several grip linkages that may be finger-held and manipulated to provide highly dexterous, precise movements of a robotic surgical tool of a surgical robotic system. The grip linkages can be mounted on a device body that contains a tracking sensor to generating an input signal used to control movement of an actuator that moves the robotic surgical tool. The grip linkages can be squeezed between an open position and a closed position, and the robotic surgical tool can make corresponding movements. For example, the robotic surgical tool can include a grasper, and jaws of the grasper can move between an open position and a closed position to grasp tissue. In the closed position, the grip linkages can lock into a latched position, and thus, the jaws of the grasper can remain closed without requiring the user to continually squeeze the grip linkages. Accordingly, the UID can be used to provide highly dexterous and precise control of the robotic surgical tool.

Referring to FIG. 1, this is a pictorial view of an example surgical robotic system 100 in an operating arena. The robotic system 100 includes a user console 120, a control tower 130, and one or more surgical robotic arms 112 at a surgical robotic platform 111, e.g., a table, a bed, etc. The system 100 can incorporate any number of devices, tools, or accessories used to perform surgery on a patient 102. For example, the system 100 may include one or more surgical tools 104 used to perform surgery. A surgical tool 104 may be end effector that is attached to a distal end of a surgical arm 112, for executing a surgical procedure.

Each surgical tool 104 may be manipulated manually, robotically, or both, during the surgery. For example, surgical tool 104 may be a tool used to enter, view, or manipulate an internal anatomy of patient 102. In an embodiment, surgical tool 104 is a grasper that can grasp tissue of patient 102. Surgical tool 104 may be handled manually, by a bedside operator 106; or it may be manipulated robotically, via actuated movement of the surgical robotic arm 112 to which it is attached. Robotic arms 112 are shown as a table-mounted system, but in other configurations the arms 112 may be mounted in a cart, ceiling or sidewall, or in another suitable structural support.

Generally, a remote operator 107, such as a surgeon or other operator, may use the user console 120 to remotely manipulate the arms 112 and/or surgical tools 104, e.g., by teleoperation. The user console 120 may be located in the same operating room as the rest of the system 100, as shown in FIG. 1. In other environments however, the user console 120 may be located in an adjacent or nearby room, or it may be at a remote location, e.g., in a different building, city, or country. The user console 120 may comprise a seat 122, foot-operated controls 124, one or more handheld user interface devices, UIDS 126, and at least one user display 128 that is configured to display, for example, a view of the surgical site inside patient 102. In the example user console 120, remote operator 107 is sitting in seat 122 and viewing the user display 128 while manipulating a foot-operated control 124 and a handheld UID 126 in order to remotely command the arms 112 and manipulate the surgical tools 104 (that are mounted on the distal ends of the arms 112). Foot-operated control(s) 124 can be foot pedals, such as seven pedals, that generate motion control signals when actuated. User console 120 may include one or more additional interface devices (FIG. 12), such as a keyboard or a joystick, to receive manual inputs to command operations of user console 120 or surgical robotic system 100.

In some variations, bedside operator 106 may also operate system 100 in an "over the bed" mode, in which bedside operator 106 (user) is now at a side of patient 102 and is simultaneously manipulating a robotically-driven tool (end effector attached to arm 112), e.g., with a handheld UID 126 held in one hand, and a manual laparoscopic tool. For example, the bedside operator's left hand may be manipulating the handheld UID 126 to command a robotic component, while the bedside operator's right hand may be manipulating a manual laparoscopic tool. Thus, in these variations, bedside operator 106 may perform both robotic-assisted minimally invasive surgery and manual laparoscopic surgery on patient 102.

During an example procedure (surgery), patient 102 is prepped and draped in a sterile fashion to achieve anesthesia. Initial access to the surgical site may be performed manually while the arms of the robotic system 100 are in a stowed configuration or withdrawn configuration (to facilitate access to the surgical site). Once access is completed, initial positioning or preparation of the robotic system including its arms 112 may be performed. Next, the surgery proceeds with the remote operator 107 at the user console 120 utilizing the foot-operated controls 124 and the UIDs 122 to manipulate the various end effectors and perhaps an imaging system, to perform the surgery. Manual assistance may also be provided at the procedure bed or table, by sterile-gowned bedside personnel, e.g., bedside operator 106 who may perform tasks such as retracting tissues, performing manual repositioning, and tool exchange upon one or more of the robotic arms 112. Non-sterile personnel may also be present to assist remote operator 107 at the user console 120. When the procedure or surgery is completed, the system 100 and/or user console 120 may be configured or set in a state to facilitate post-operative procedures such as cleaning or sterilization and healthcare record entry or printout via user console 120.

In one embodiment, remote operator 107 holds and moves UID 126 to provide an input command to move a robot arm actuator 114 in robotic system 100. UID 126 may be communicatively coupled to the rest of robotic system 100, e.g., via a console computer system 110. UID 126 can generate spatial state signals corresponding to movement of UID 126, e.g., position and orientation of the handheld housing of the UID, and the spatial state signals may be input signals used to control a motion of the robot arm or tool actuator 114. For example, the tracking sensor can generate an input pose signal for controlling spatial motion of a corresponding surgical tool. Robotic system 100 may use control signals derived from the spatial state signals, to control proportional motion of actuator 114. In one embodiment, one or more processors, e.g., a console processor of console computer system 110 receives the spatial state signals and generates the corresponding control signals. Based on these control signals, which control how the actuator 114 is energized to move a segment or link of arm 112, the movement of a corresponding surgical tool that is attached to the arm may mimic the movement of UID 126. Similarly, interaction between remote operator 107 and UID 126 can generate for example a grip control signal that causes a jaw of a grasper of the surgical tool to close and grip the tissue of patient 102. For example, the one or more processors can be configured to control the surgical tools based on at least one of the input pose signal and a grip signal, as described below.

The motion of UID 126 may alternatively be provided to control other aspects of surgical robotic system 100. For example, gestures detected by a finger clutch may generate a clutch signal to pause the motion of actuator 114 and the corresponding surgical tool 104. For example, when a user touches the finger clutch of UID 126 with a finger, the finger clutch may generate a clutch signal, and the clutch signal may be an input signal to pause the motion of actuator 114. Similarly, one or more capacitive sensing pads may be located on UID 126, and the user may touch the capacitive sensing pads to command a camera view of an endoscope, a cursor on a display of user console 120, etc., while performing a diagnostic, surgical, laparoscopic, or minimally invasive surgical procedure, or another robotic procedure.

Surgical robotic system 100 may include several UIDs 126, where respective control signals are generated for each UID that control the actuators and the surgical tool (end effector) of a respective arm 112. For example, remote operator 107 may move a first UID 126 to command the motion of actuator 114 that is in a left robotic arm, where the actuator responds by moving linkages, gears, etc., in that arm 112. Similarly, movement of a second UID 126 by remote operator 107 commands the motion of another actuator 114, which in turn moves other linkages, gears, etc., of the robotic system 100. Robotic system 100 may include a right arm 112 that is secured to the bed or table to the right side of the patient, and a left arm 112 that is at the left side of the patient. An actuator 114 may include one or more motors that are controlled so that they drive the rotation of a joint of arm 112, to for example change, relative to the patient, an orientation of an endoscope or a grasper of the surgical tool that is attached to that arm. Motion of several actuators 114 in the same arm 112 can be controlled by the spatial state signals generated from a particular UID 126. UIDs 126 can also command motion of respective surgical tool graspers. For example, each UID 126 can generate a respective grip signal to control motion of an actuator, e.g., a linear actuator, that opens or closes jaws of the grasper at a distal end of the surgical tool to grip tissue within patient 102.

In some aspects, the communication between platform 111 and user console 120 may be through a control tower 130, which may translate user commands that are received from user console 120 (and more particularly from console computer system 110) into robotic control commands that transmitted to arms 112 on robotic platform 111. The control tower 130 may also transmit status and feedback from platform 111 back to user console 120. The communication connections between the robotic platform 111, user console 120, and control tower 130 may be via wired and/or wireless links, using any suitable ones of a variety of data communication protocols. Any wired connections may be optionally built into the floor and/or walls or ceiling of the operating room. Robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
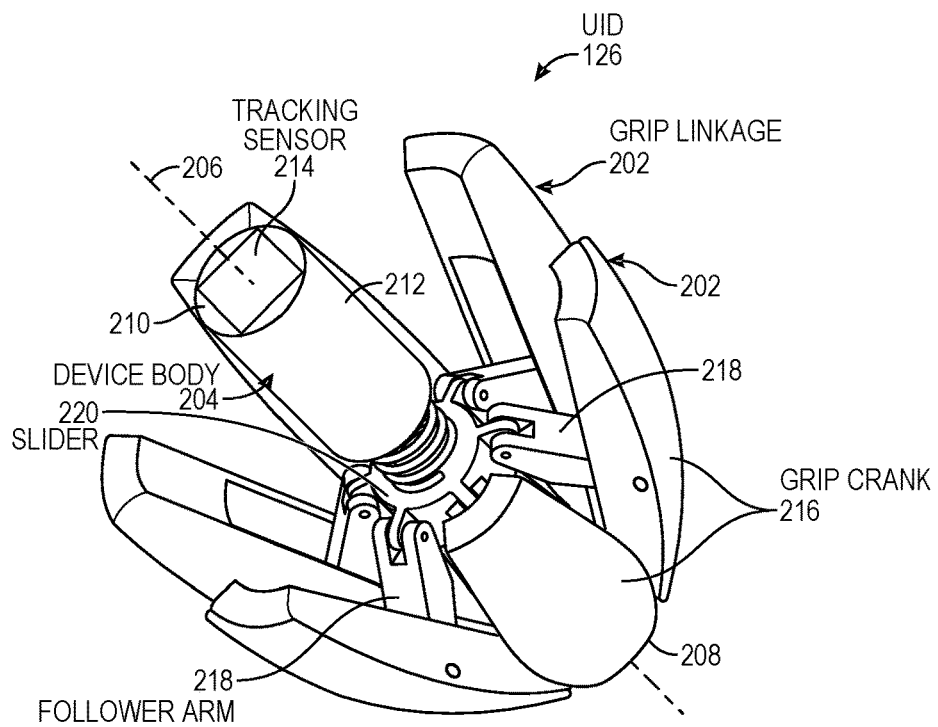
FIG. 2 is a perspective view of a user interface device in an open configuration, in accordance with an embodiment.

Referring to FIG. 2, a perspective view of a user interface device in an open configuration is shown in accordance with an embodiment. A UID 126 can include a gripping structure to be held by a user, e.g., remote operator 107. For example, UID 126 may include several grip linkages 202 extending outward from a centrally located device body 204. The user may hold portions of the grip linkages 202 between several fingers and move UID 126 within a workspace. The workspace may be a range of reach of the user.

In an embodiment, device body 204 extends in a longitudinal direction along a central axis 206. For example, device body 204 may extend longitudinally from a proximal end 208 that is normally cupped within a hand of user 107 when the user is holding gripping linkages. Device body 204 may extend to a distal end 210 having a forward-facing surface. Device body 204 can be segmented into several portions. A distal portion of device body 204 may include a device head 212 having an outer surface extending around central axis 206. The outer surface of device head 212 can be cylindrical, and may surround a cavity. The cavity within device head 212 can receive a tracking sensor 214 used to track movement of UID 126. More particularly, tracking sensor 214 may be mounted within device body 204. Tracking sensor 214 can be fixed to device head 212, and thus, tracking sensor 214 may experience the same movement as device head 212.

As described below, tracking sensor 214 can be configured to track movement of the device body of UID 126 and generate an input spatial state signal to control motion of the surgical tool. The input spatial state signal can be generated in response to movement of device body 204. Tracking sensor 214 can detect a position and/or orientation of device body 204 when user 107 moves UID 126, and the detected position and/or orientation may be correlated to a control of a surgical robotic system 100. For example, tracking sensor 214 may detect motion in several degrees of freedom, e.g., translation in one or more directions, rotation about one or more axes, or tilting relative to one or more axes, of device body 204 within the workspace. The tracking sensor 214 may include an accelerometer and/or a gyroscope or other inertial sensors. The tracking sensor 214 may include a six-degree-of-freedom position sensor. For example, the position sensor can be an electromagnetic tracking sensor including components, e.g., coils, having a parameter responsive to a surrounding magnetic field and measurable, e.g., by a tracking system, to determine a position or orientation of the sensor. The tracking sensor 214 may include an optical tracker component having marker patterns identifiable in an image to determine a position or orientation of the sensor. The tracking system can be incorporated into user console 120, and may be connected to tracking sensor 214 by a wired or wireless link. Detected movement of UID 126 within the workspace can cause a corresponding movement, such as a grip motion or a grasp motion, of an end effector or tool, e.g., a grasping movement of a grasper or a gripping movement of a jaw, of the surgical robotic system 100.

UID 126, which is handled by remote operator 107 to command surgical tool 104 and/or arms 112, can be ergonomic. For example, UID 126 can include several, e.g., at least three, grip linkages 202 extending radially outward from central axis 206 at angles to one another. Accordingly, user 107 can comfortably hold grip linkages 202 between an extended thumb, index finger, and middle finger. Each gripping linkage can include a grip crank 216 having an exterior gripping surface to be pressed by a finger of user 107. The grip cranks 216 can be pivotally coupled to device body 204 at a corresponding pivot (FIG. 5) such that pressure applied to grip crank 216 by the finger of user 107 can move grip crank 216 radially inward toward device body 204. For example, grip linkages 202 can be connected to device body 204 near a proximal end 208.

Movement of the grip cranks 216 can cause movement of other components of grip linkages 202. Each grip linkage 202 can be a slider-crank mechanism, and the grip linkages 202 can have grounds (pivots of grip cranks 216) that are linked to device body 204. Each grip linkage 202 can include a follower arm 218 pivotally coupled to grip crank 216 at a corresponding pivot. Furthermore, follower arm 218 can extend radially inward from grip crank 216 to a slider 220. Follower arm 218 can be pivotally coupled to slider 220 at a corresponding pivot joint. Whereas grip cranks 216 may be grounded to device body 204 at pivot joints, slider 220 may be slidably coupled to device body 204.

Figure 3:
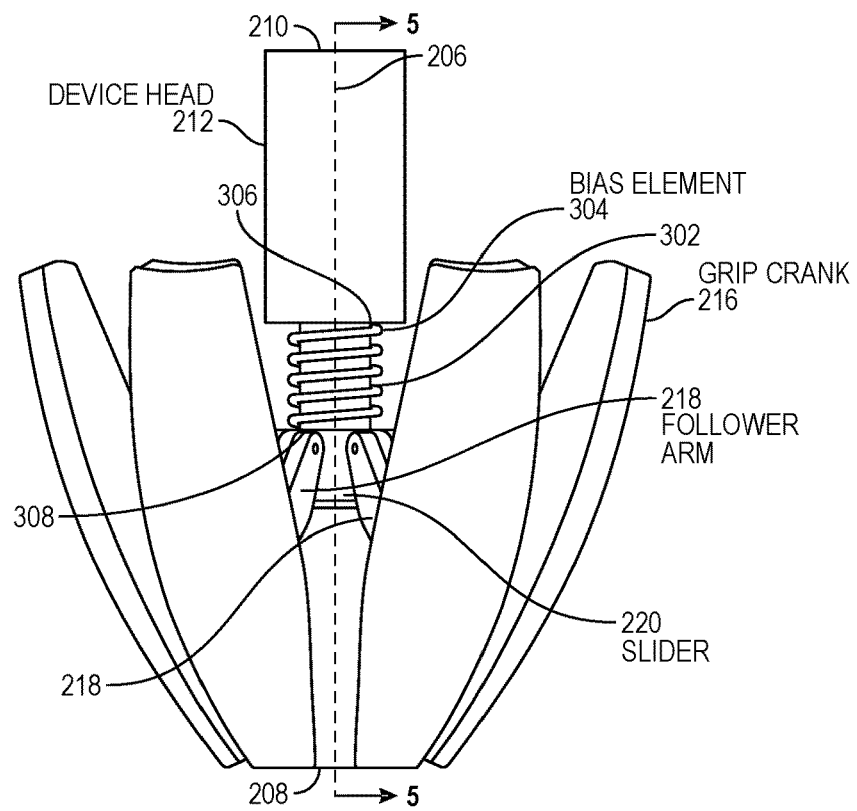
FIG. 3 is a side view of a user interface device in an open configuration, in accordance with an embodiment.

Referring to FIG. 3, a side view of a user interface device in an open configuration is shown in accordance with an embodiment. Slider 220 may be slidably coupled to a shaft portion of device body 204. The shaft portion can include a body surface 302, and slider 220 may be mounted on body surface 302. By way of example, slider 220 may be a collar having an inner channel that includes a cross-sectional profile that is slightly larger than an outer profile of body surface 302. The collar may have a sliding fit over body surface 302 to connect slider 220 to device body 204 at a slider body joint. Accordingly, slider 220 may move along central axis 206 between distal end 210 and proximal end 208 of device body 204.

The grip linkages 202 can share a same slider 220. For example, the gripping mechanism may have an array of three or more interconnected grip linkages 202. The interconnected grip linkages 202 can have respective grip cranks 216 connected to device body 204 at respective grounds, and the grip linkages 202 may have respective follower arms 218 connected to a same slider 220. Accordingly, when one of the grip cranks 216 moves radially inward towards device body 204, the corresponding grip linkage 202 can push slider 220 distally to pull the other grip cranks 216 toward device body 204. That is, the grip linkages 202 may be interconnected such that actuation of any one grip crank 216 results in an actuation of all of the grip cranks 216, and a corresponding movement of slider 220.

Motion of slider 220 may be opposed by a bias element 304. Bias element 304 can have a first end 306 and a second end 308 capable of moving relative to one another. Bias element can be a passive or active element. For example, bias element 304 may be a passive element, such as a return spring having ends that move relative to each other. The return spring can be a compression spring or a tension spring, depending on a mounting position of the spring. For example, the ends of the return spring can move toward each other (e.g., when the spring is storing energy in the case of a compression spring, or when the spring is releasing energy in the case of a tension spring) and away from each other (e.g., when the spring is releasing energy in the case of the compression spring, or when the spring is storing energy in the case of the tension spring). The return spring can be preloaded between device body 204 and slider 220. For example, first end 306 of bias element 304 may press against or be otherwise connected to a proximal surface of device head 212, and second end 308 may press against or be otherwise connected to a distal surface of slider 220. Bias element 304 may move slider 220 toward and/or away from first end 306. For example, when bias element 304 is a compression spring and user 107 has squeezed grip cranks 216 to a closed position, if user 107 releases grip cranks 216, bias element 304 can expand to push slider 220 proximally and to force grip cranks 216 radially outward toward an open position. Similarly, when bias element 304 is a tension spring mounted between a proximal surface of slider 220 and proximal end 208, bias element 304 can pull slider 220 from an end-of-travel position in the closed configuration of grip linkages 202 to an open position in the open configuration of grip linkages 202. More particularly, when user 107 releases grip cranks 216 from the closed position, bias element 304 can force slider 220 and grip linkages 202 to the open position.

In an embodiment, bias element 304 is an active element, such as a linear actuator having first end 306 connected to device body 204 and second end 308 connected to slider 220. Linear actuator can include a linear motor mounted in a core of UID 126. Linear motor can drive first end 306 and second end 308 toward or away from each other to move slider 220 distally and proximally relative to device head 212. As described above with respect to the return spring, linear actuator can exert a restorative force on slider 220 to move slider 220 and grip linkages 202 toward the open position when user 107 releases grip cranks 216 from the closed position. Furthermore, linear actuator can provide force feedback to user 107. The force feedback or motion provided to user can be a tactile feedback mechanism, e.g., haptic feedback, corresponding to a gripping force being applied to a target tissue site. By driving against slider 220, linear actuator can give a sensation to user 107 that grip cranks 216 are being squeezed onto something. More particularly, linear actuator can provide a resistive force to simulate the resistance that user 107 would feel if the user were manually squeezing, e.g., with forceps, the tissue of patient 102. Linear actuator can drive grip cranks 216 against the user's fingers with an amount of force to indicate the amount of force that is being applied to tissue by the user. Accordingly, user 107 can know how much force the instrument is applying to tissue based on the reactive force applied by linear actuator to the user's fingers through grip linkages 202.

Figure 4:
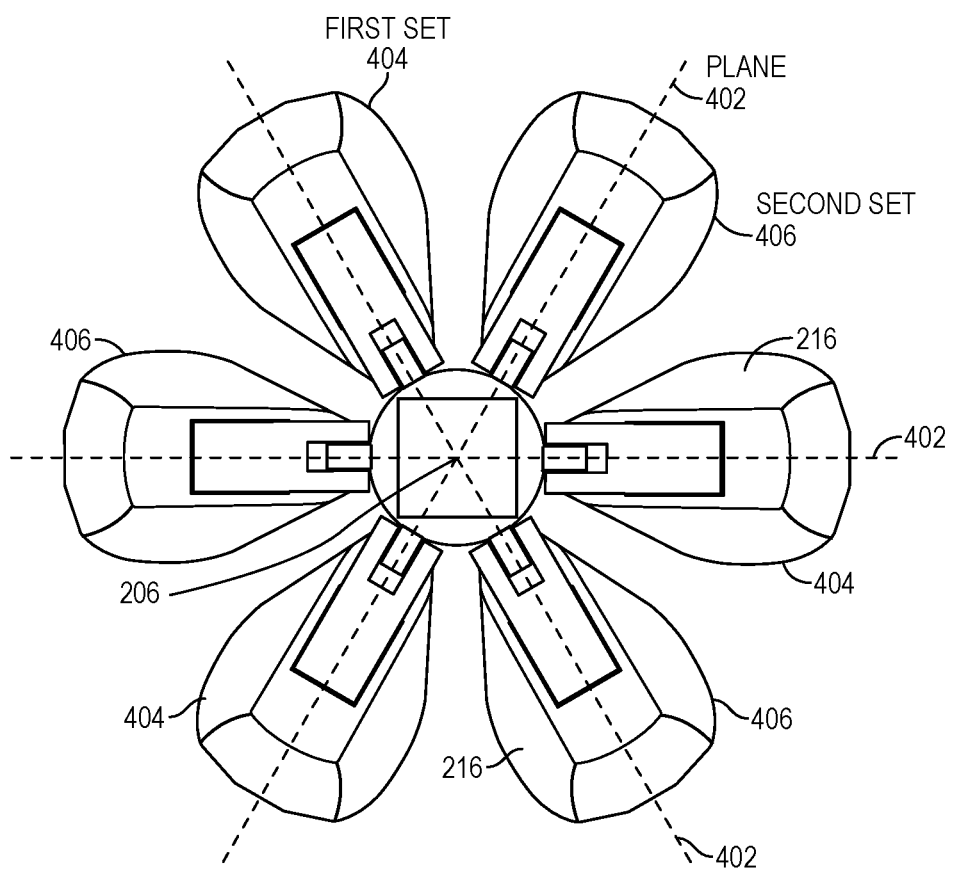
FIG. 4 is an end view of a user interface device in an open configuration, in accordance with an embodiment.

Referring to FIG. 4, an end view of a user interface device in an open configuration is shown in accordance with an embodiment. Each grip crank 216 can extend from device body 204 along a respective plane 402. The planes 402 can extend longitudinally and intersect along a line that is parallel to central axis 206. For example, planes 402 may intersect along central axis 206. In an embodiment, grip linkages 202 are rotationally symmetric about central axis 206. Accordingly, planes 402 can be equiangular about central axis 206. By way of example, as shown in FIG. 4, when UID 126 includes a circular array of six grip linkages 202, the grip linkages 202 may be distributed along six planes 402 that are circumferentially separated from each other by an angle of 60 degrees. the gripping structure is therefore a radially symmetric mechanism with respect to central axis 206.

Grip linkages 202 of UID 126 may be broken into symmetric sets. In an embodiment, the gripping structure includes a first set of grip linkages 404 distributed uniformly about central axis 206. More particularly, first set of grip linkages 404 may be a first circular array of three or more grip linkages 202. When first set includes three grip linkages 202, a respective grip crank 216 of each grip linkage 202 may extend along the respective plane 402 that is separated from the other planes 402 by 120 degrees. UID 126 can include a second set of grip linkages 406. Second set of grip linkages 406 may be distributed uniformly about central axis 206. Second set of grip linkages 406 may be a second circular array of three or more grip linkages 202, and the second circular array may be alternately located relative to central axis 206 with respect to the first circular array of first set of grip linkages 404. More particularly, each grip crank 216 of the second set may extend between a pair of adjacent grip cranks 216 of the first set. Accordingly, second set 406 includes at least one grip crank 216 extending from device body 204 between respective planes 402 of first set of grip linkages 404. As described below, each set of grip linkages can generate signals used to control a different non-gripping function of surgical robotic system 100. The sets may nonetheless open and close in unison to generates signals to control a gripping function of surgical robotic system 100 when user 107 squeezes on any of grip cranks 216. That is, when user 107 squeezes grip cranks 216, grip linkages 202 can move toward the closed position and a location of slider 220 along central axis 206 may change. The change in slider position may be detected as an input to cause a corresponding output of a gripper control signal.

Figure 5:
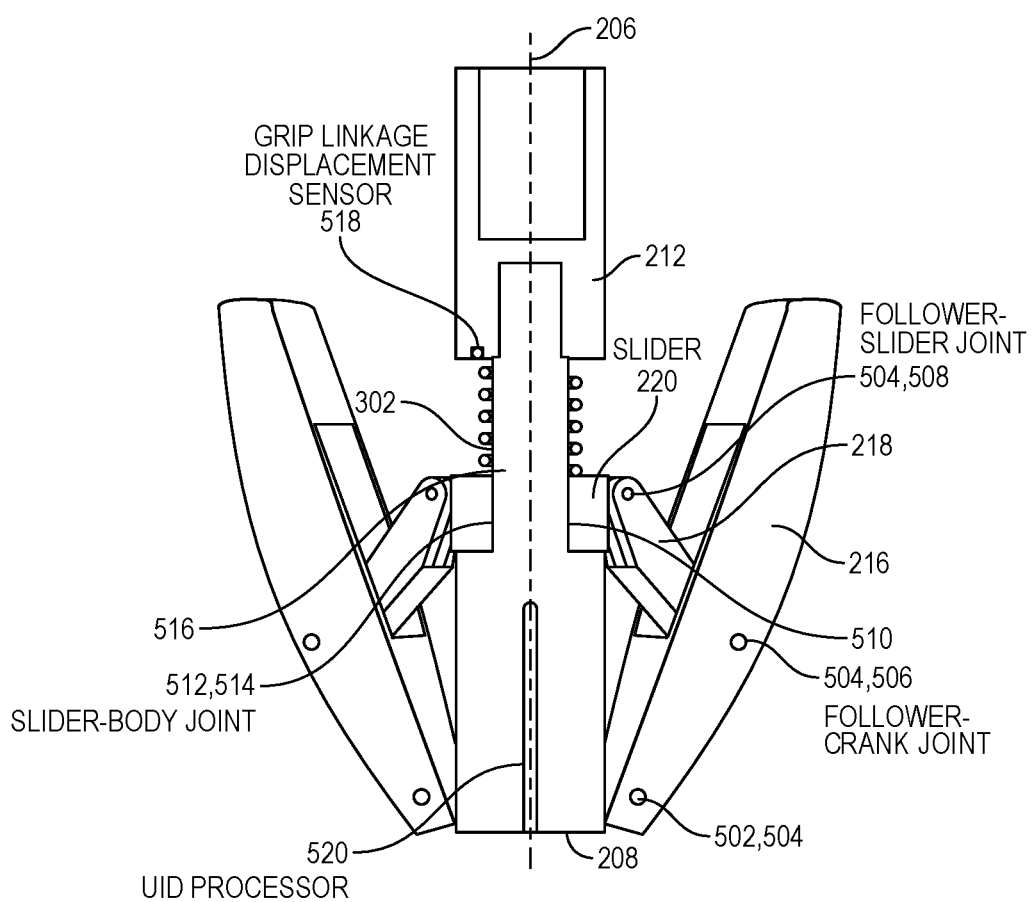
FIG. 5 is a sectional view, taken about line 5-5 of FIG. 4, of a user interface device in an open configuration, in accordance with an embodiment.

Referring to FIG. 5, a sectional view, taken about line 5-5 of FIG. 3, of a user interface device in an open configuration is shown in accordance with an embodiment. Each grip linkage 202 of UID 126 can be a slider-crank mechanism interconnected by a common slider 220. As described above, grip crank 216 may be connected to device body 204 near a proximal end 208 at a device-crank joint 502. Device-crank joint 502 may be a revolute joint 504 having a single degree of freedom (rotational about the pivot axis) to allow grip crank 216 to pivot radially inward and radially outward relative to central axis 206. Follower arm 218 can bridge between grip crank 216 and slider 220. More particularly, follower arm 218 may be connected to grip crank 216 at a follower-crank joint 506, and follower arm 218 may be connected to slider 220 at a follower-slider joint 508. Like device-crank joint 502, follower-crank joint 506 and follower-slider joint 508 can be revolute joints 504 to allow follower arm 218 to pivot and change angles with respect to central axis 206. For example, as follower arm 218 pivots into an orientation that is more parallel to central axis 206, slider 220 may advance distally along a body surface 302 of device body 204. By contrast, as follower arm 218 pivots into an orientation that increases an angle between central axis and a length of arm 218, slider 220 may advance proximally along body surface 302.

Body surface 302 may be an exterior surface of a device shaft 516. Device shaft 516 can be a cylindrical shaft portion of device body 204 extending between device head 212 and proximal end 208. Device shaft 516 can extend along central axis 206, and thus, body surface 302 may extend around central axis 206. Slider 220 may include a collar extending around central axis 206. An interface between slider 220 and body surface 302 can be a prismatic joint 514. More particularly, slider 220 may be connected to body surface 302 at a slider-body joint 512, and slider-body joint 512 may be a prismatic joint 514. Rotation of slider 220 about central axis 206 may be constrained by follower arms 218, and thus, slider 220 may have a single degree of freedom (axial) along central axis 206.

Displacement of slider 220 along central axis 206 can be monitored. In an embodiment, UID 126 includes a grip linkage displacement sensor 518. Displacement sensor 518 can be a displacement detection sensor to detect and/or measure a position or motion of slider 220 over body surface 302. For example, grip linkage displacement sensor 518 may be an optical displacement sensor that emits radiant energy toward a distal surface of slider 220. Grip linkage displacement sensor 518 can detect energy reflected from the distal surface. The sensor can determine a longitudinal distance between the distal surface of slider 220 and device head 212 based on the received energy. More particularly, grip linkage displacement sensor 518 can determine an axial position of slider 220 on body surface 302 using optical sensing techniques. Other sensor types may be used to determine the axial location of slider 220 on device shaft 516. Grip linkage displacement sensor 518 may be configured to generate an output signal based on the displacement or position of slider 220. The output signal may be termed a grip signal, given that slider 220 movement corresponds to movement of grip cranks 216, the grip signal may be generated in response to movement of grip linkages 202. Thus, when user 107 squeezes grip linkages 202, the grip signal may be generated and output to surgical robotic system 101 to control movement of a portion of surgical tool 104, e.g., jaws of a grasper. Grip linkage displacement sensor 518 may be electrically connected to other electronics mounted within device body 204. For example, a power supply within device body 204 may power grip linkage displacement sensor 518. Similarly, grip linkage displacement sensor 518 may communicate data to a UID processor 520 mounted within device body 204. UID processor 520 can process the sensor data and communicate corresponding signals, e.g., the grip signal, to computer system 110.

Figure 8:
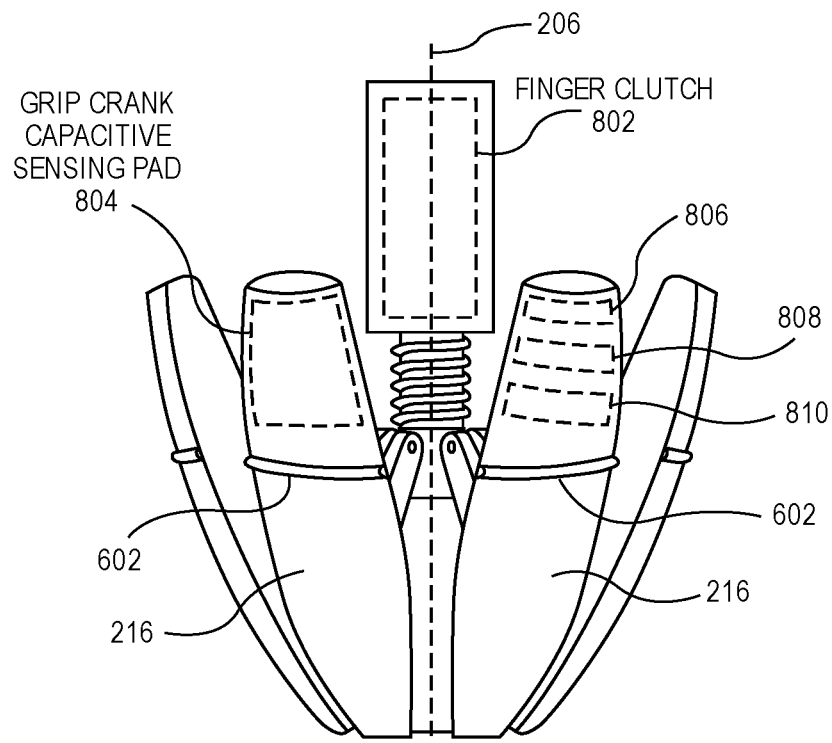
FIG. 8 is a side view of several touch sensitive surfaces of a user interface device, in accordance with an embodiment.

UID 126 may include an internal volume to receive various electronics, including UID processor 520. UID processor 520 may encompass circuitry for analog and digital signal processing, including sensing amplifier circuits and analog-to-digital conversion circuitry used to interface with the capacitive sensor, and logic circuitry including programmable logic or a programmable digital processor. UID processor 520 may be mounted on a printed circuit board having various sensor terminals to connect UID processor 520 to device sensors, e.g., tracking sensor 214 or grip linkage displacement sensor 518. A battery may be mounted on the printed circuit board to power electronic components of UID 126. An electrical wire (not shown) may extend along central axis 206 through central bores of each component of UID 126 to connect to UID processor 520. For example, the electrical wire may extend along central axis 206 from tracking sensor 214 or grip linkage displacement sensor 518 through device shaft 516 and device head 212 to attach to a terminal on UID processor 520 or the printed circuit board. UID processor 520 may be electrically connected to other sensors, e.g., a conductive pad or a finger clutch (FIG. 8). The electrical wire may conduct a capacitance signal to UID processor 520 that may be compared to a ground terminal. The ground terminal may be on UID processor 520 or the printed circuit board. Accordingly, UID processor 520 may be configured to detect a change of capacitance of the conductive pad or the finger clutch to trigger the functions described below.

Figure 6:
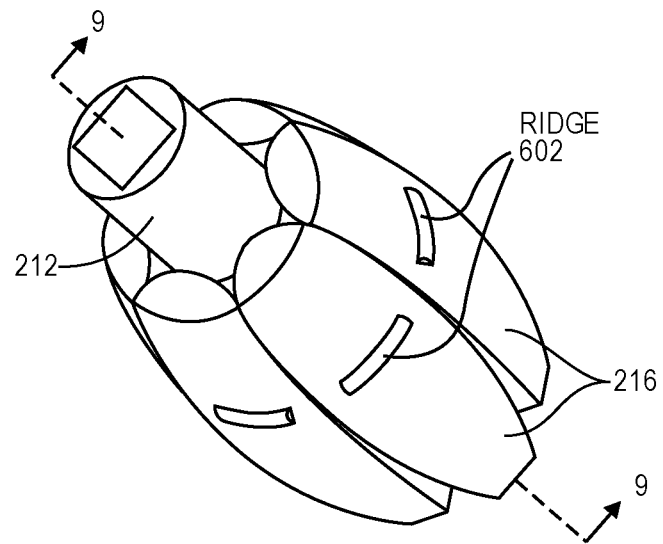
FIG. 6 is a perspective view of a user interface device in a closed configuration, in accordance with an embodiment.

Referring to FIG. 6, a perspective view of a user interface device in a closed configuration is shown in accordance with an embodiment. When user 107 squeezes grip cranks 216 to a closed position, laterally facing surfaces of the grip cranks 216 can abut each other. The abutting grip cranks can have exterior surfaces that combine to form a generally bulbous outer profile. More particularly, an outer envelope defining the exterior surfaces of grip cranks 216 can have one or more rounded or bulbous surface contours. For example, the envelope may be generally ovoid or egg-shaped, or it may be a ellipsoid. In the closed configuration, UID 126 may have a circumferential ridge 602 formed by a combination of ridge arcs located on each grip crank 216. Ridge 602 may provide a tactile datum, i.e., a feature to indicate a known grip location. That is, ridge 602 can be a reference feature for the user's grip.

The envelope of grip cranks 216 in the closed configuration may include a surface of revolution having a surface contour revolved about central axis 206. In one instance, the envelope defines an ellipsoid and central axis 206 may be the longitudinal or major axis of the ellipsoid. A portion of the envelope in front of circumferential ridge 602 may be shorter and have a less gradual contour or taper than a portion of the envelope in back of ridge 602. Thus, the distal portion and the proximal portion of the envelope may have different radii of curvatures measured from a point where central axis 206 of UID 126 intersects a transverse plane on which ridge 602 is located in the closed configuration. Such a profile can provide a comfortable gripping surface for user 107. Furthermore, the surface of revolution provided by the combined exterior surfaces of grip cranks 216 in the closed configuration may be better for finger manipulation. That is, when UID 126 is closed, the surface of revolution allows UID 126 to be rolled between the fingers of user 107 to generate signals to control a twisting motion of an end effector of robotic arm 112 and/or gripper jaws of surgical tool 104. Accordingly, the surface of revolution of UID 126 in the closed configuration allows for highly dexterous, precise movements and control of surgical robotic system 100.

UID 126 affords highly dexterous, precise movements in the opened, or partially closed configurations, also. The curved outer surface of grip cranks 216 can be rolled between the fingers of user in all configurations, which can provide a comfortable gripping surface.

Figure 7:
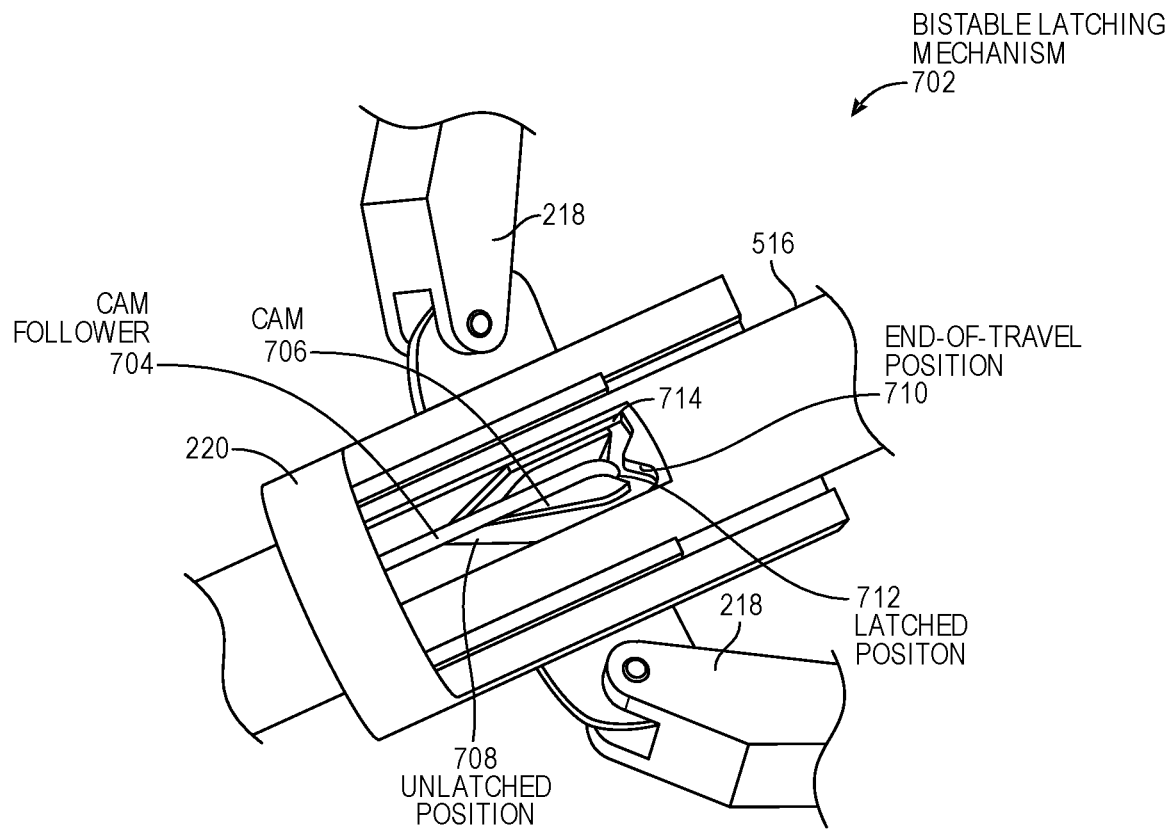
FIG. 7 is a perspective view of a bistable latching mechanism of a user interface device, in accordance with an embodiment.

Referring to FIG. 7, a perspective view of a bistable latching mechanism of a user interface device is shown in accordance with an embodiment. User 107 may need to maintain grip cranks 216 at the closed position for a period of time while the surgery is being performed. For example, user 107 may need to lock gripper jaws of surgical tool in a closed state over an extended period of time. To prevent hand fatigue, UID 126 may include a bistable latching mechanism 702 to lock grip cranks 216 in the closed position until user 107 is ready to release them back toward the unlocked state, e.g., the open position.

UID 126 may internally incorporate bistable latching mechanism 702. For example, components of bistable latching mechanism 702 may be between an interior surface of slider 220 and an exterior surface of device body 204, e.g., device shaft 516. Accordingly, FIG. 7 may be a partial sectional view to reveal the exterior surface of device body 204 beneath the interior surface of slider 220.

Bistable latching mechanism 702 may incorporate a push-push mechanism. The push-push mechanism can lock grip linkages 202 in the closed configuration when the grip cranks 216 are fully closed and then relaxed. The push-push mechanism can unlock grip linkages 202 to release UID 126 to the open configuration when grip cranks 216 are again fully closed from the closed configuration and then released. Thus, bistable latching mechanism 702 may be a mechanism that is squeezed to lock, and squeezed again to release.

In an embodiment, bistable latching mechanism 702 can include a cam follower 704 that moves along a cam 706. Cam follower 704 and cam 706 may be incorporated into slider 220 or device body 204. Cam follower 704 and cam 706, however, may not be incorporated in a same component, e.g., not both incorporated in slider 220 or device body 204. By way of example, cam 706 may be integrated in device shaft 516 and cam follower 704 may be mounted on slider 220 that rides over device shaft 516. Cam follower 704 can be located between the interior surface of slider 220 and the exterior surface of device shaft 516. Cam follower 704 and cam 706 may be movable relative to each other.

Cam follower 704 can include a longitudinal cantilever portion extending parallel to central axis 206. Cam follower 704 may also include a prong portion extending from an end of the cantilever portion radially inward toward central axis 206. The prong portion can extend into cam 706. More particularly, cam 706 may include a groove formed in an exterior surface of device shaft 516, and the prong portion may be located within the groove.

The groove of cam 706 may extend along a looping path. For example, the path may have an unlatched position 708 at a proximalmost location of the groove, an end-of-travel position 710 at a distalmost location of the groove, and a latched position 712 at a location of the groove between the proximalmost location and the distalmost location. The path can extend in a counterclockwise direction from unlatched position 708 to end-of-travel position 710 and then to latched position 712. Continuing along the groove in the counterclockwise direction, the path returns to the starting point at unlatched position 708. Accordingly, the path may be a closed path.

Cam follower 704 may move around the groove when the grip linkages 202 move between the closed configuration and the open configuration. For example, cam follower 704 can move between unlatched position 708, end-of-travel position 710, and latched position 712 when user 107 squeezes the grip linkages 202. In the open configuration, with the grip cranks 216 radially extended, the prong portion of cam follower 704 may be located at unlatched position 708 of groove. As user 107 pinches grip cranks 216 between several fingers, grip cranks 216 pivot toward device body 204 between an open configuration (FIG. 2) and a closed configuration (FIG. 6). Cam follower 704 can move along groove between unlatched position 708 and end-of-travel position 710 as UID 126 transitions to the closed configuration. As user 107 relaxes the grip on grip cranks 216, allowing the return spring 304 to bias slider 220, grip cranks 216 pivot away from device body 204 between the closed position and a locked position. That is, as cam follower 704 moves from end-of-travel position 710 to latched position 712, grip cranks 216 move radially outward to the locked position. Accordingly, grip crank 216 may be nearer to central axis 206 in the closed position than in the locked position.

The grip linkage 202 may be in the closed configuration when grip cranks 216 are at either of the closed position or the locked position. The radial movement of grip cranks 216 from the closed position to the locked position may be negligible. For example, the exterior surfaces of grip cranks 216 may combine to form an ellipsoid envelope at both the closed position and the locked position. At the locked position, however, user 107 is not required to squeeze grip cranks 216 to maintain grip linkages 202 in the closed configuration. Accordingly, user 107 may manipulate UID 126 by twisting or rolling grip cranks 216 when the prong of cam follower 704 is at latched position 712.

To unlatch grip cranks 216, user 107 can squeeze grip cranks 216 toward central axis 206. Radially inward movement of grip cranks 216 when the prong portion of cam follower 704 is at latched position 712 can force cam follower 704 along the groove of cam 706 in the counterclockwise direction. The prong can be forced to a second end-of-travel position 714 distal to latched position 712. When the prong is at second end-of-travel position 714, grip cranks 216 can be at the closed position. When grip cranks 216 are relaxed from the closed position, cam follower 704 may follow groove between the second end-of-travel position 714 to unlatched position 708.

The segments of the groove in cam 706 may be at different elevations to bias cam follower 704 in a certain direction. For example, when cam follower 704 reaches the second end-of-travel position 714, a floor of the groove may drop to cause cam follower 704 to drop onto a segment of the groove between second end-of-travel position 714 and unlatched position 708. When cam follower 704 returns to unlatched position 708, grip cranks 216 may be at the open position again. At the open position, grip cranks 216 are farther from central axis 206 than at the locked position. That is, grip crank 216 may be nearer to central axis 206 at the locked position than at the open position.

Bistable latching mechanism 702 shown in FIG. 7 and described above includes one type of push-push mechanism that provides bistable latching of grip linkages 202. Other push-push mechanisms may be used. In any case, the push-push mechanism can include a mechanism that locks itself in the closed configuration when user 107 squeezes grip cranks 216 to an end-of-travel, and when user 107 squeezes the mechanism again, grip cranks 216 are released toward the open position.

Bistable latching mechanism 702 can include features that indicate states of UID 126 to user 107. For example, bistable latching mechanism 702 may include a snap feature to indicate that cam follower 704 has reached the end-of-travel position 710. An audible snapping sound, or a physical tactile vibration associated with snapping, may be emitted when the prong portion of cam follower 704 descends from a higher groove floor to a lower groove floor at end-of-travel position 710. The clicking sound or sensation can indicate that end-of-travel position 710 has been reached. User 107 then knows that grip cranks 216 can be released to lock UID 126 in the closed configuration. Similar snap features may be implemented at other positions of grip cranks 216. For example, a snap feature may click when cam follower 704 reaches second end-of-travel position 714 to indicate to user 107 that UID 126 is unlatched and grip cranks 216 can be extended radially outward.

To perform a surgery with surgical instruments, user 107 may need to know when gripper jaws of surgical tool are completely closed. For example, surgical tool may be a needle driver having a gripper, and closing grip cranks 216 of UID 126 may map to the instrument jaws closing. Accordingly, when user 107 feels a click from the snap feature, user 107 is notified that the instrument jaws have reached an end-of-travel state, e.g., a fully clamped state.

Similar latching of grip linkages 202 can be performed using the linear actuator described above. For example, the linear actuator may be controlled to stop actuation when slider 220 is determined to reach an end-of-travel position along device shaft 516. When user 107 squeezes grip cranks 216 again, slider 220 can advance to the end-of-travel position, which may be detected by UID processor 520, and the linear actuator may be controlled to return slider 220 to a more proximal position and allow grip cranks 216 to expand radially outward. Accordingly, bistable latching of UID 126 can be performed mechanically and/or electromechanically.

Referring to FIG. 8, a side view of several touch sensitive surfaces of a user interface device is shown in accordance with an embodiment. UID 126 can include several touch sensitive surfaces. The touch sensitive surfaces can include capacitive and/or conductive elements that generate a signal in response to a touch by user 107. Accordingly, by touching predetermined locations on UID 126, user 107 can command specific functions of surgical robotic system 100. The functions can be non-gripping functions.

In an embodiment, UID 126 includes a clutch mechanism to decouple movement of UID 126 from the control of the surgical robotic system 100. The clutch mechanism can be referred to as a finger clutch. The finger clutch may be so-termed because it may be actuated by a touch from a finger of user 107. In an embodiment, a finger clutch 802 may be mounted on or integrated in a region of device body 204 as indicated by the dotted line. For example, device head 212 can include finger clutch 802. Finger clutch 802 may include a touch sensitive exterior surface of device head 212 that allows user 107 to pause teleoperation for an individual instrument that is being manipulated by UID 126. That is, when user 107 touches finger clutch 802, the touch may be detected as a clutch input. In response to the clutch input, control signals corresponding to movement of UID 126 detected by the tracking sensor 214 may be discontinued. When the clutch input is removed (when the touch is ended) the movement of UID 126 may again cause a corresponding movement of the surgical robotic system 100. That is, when finger clutch 802 is unclutched, e.g., by removing a finger from finger clutch 802, UID movement may again be detected and input to the surgical robotic system 100 as a motion control input.

Finger clutch 802 of UID 126 can allow user 107 to reposition UID 126 within the workspace when a limit of the workspace has been reached. For example, by extending an arm fully from a start position in a direction while holding UID 126, user 107 may reach the limit of the workspace, e.g., an edge of the workspace. To reposition UID 126 within the workspace and allow for additional movement in the direction of the workspace edge, user 107 can touch the finger clutch 802 with an index finger to disconnect the surgical robotic system 100 from the movement of UID 126. User 107 may then move UID 126 back to the start position within the workspace and unclutch the surgical robotic system 100 by lifting the index finger from finger clutch 802. Additional movement in the first direction may then be performed by moving UID 126 to manipulate motion of surgical robotic system 100.

Figure 9:
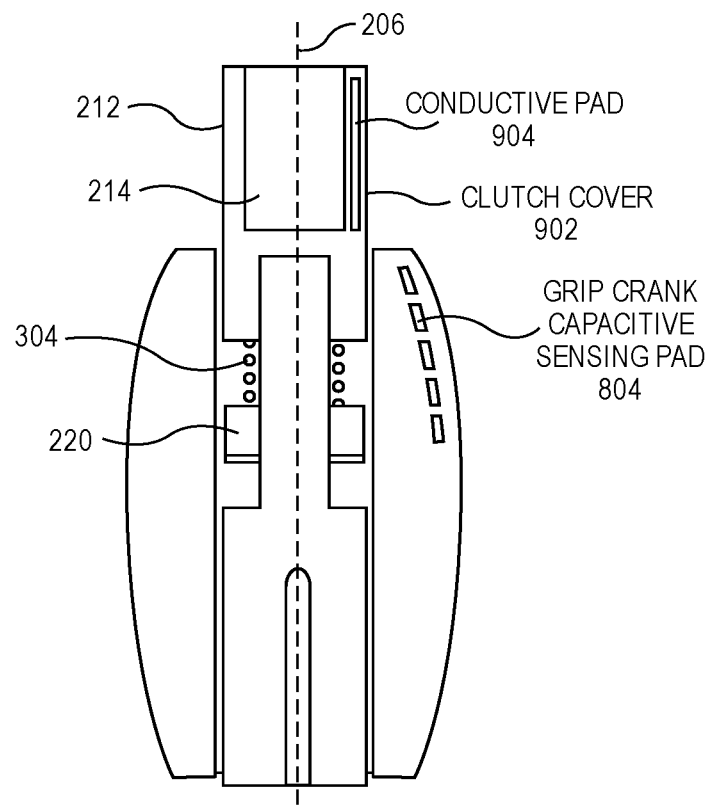
FIG. 9 is a sectional view, taken about line 9-9 of FIG. 6, of a user interface device in a closed configuration, in accordance with an embodiment.

Referring to FIG. 9, a sectional view, taken about line 9-9 of FIG. 6, of a user interface device in a closed configuration is shown in accordance with an embodiment. Finger clutch 802 can include a clutch cover 902 mounted over a conductive pad 904. Conductive pad 904 may extend around central axis 206. For example, whereas central axis 206 may extend longitudinally, an outer surface of conductive pad 904 may follow a path along a transverse plane orthogonal to longitudinal axis. The path may extend fully around central axis 206, e.g., the profile on the transverse plane may be circular. Alternatively, the path may extend partially around central axis 206, e.g., the profile may be c-shaped. In an embodiment, the profile sweeps over an angle of at least 270 degrees, where the angle is measured about central axis 206. The profile described above may be a singular transverse slice of conductive pad 904, and in an embodiment, a shape of the profile may be the same over a length of conductive pad 904. That is, each transverse slice of conductive pad 904 taken along the length of conductive pad 904 may be a same shape, e.g., circular in the case of a cylindrical conductive pad 904.

Although not shown, in one embodiment, an electrical wire may join conductive pad 904 at one end to an input of a sensing amplifier circuit (part of UID processor 520 within device body 204) at another end. The sensing amplifier circuit may produce a sensed signal that changes in accordance with the signal on the electrical wire. The signal may change as a result of the capacitance of the conductive pad 904 changing, based on a proximity of the user's finger to the conductive pad 904 or based on the touch of the user's finger on the touch sensitive portion of device head 212 over conductive pad 904. UID processor 520 may process a digitized version of a sensed signal to determine whether or not a capacitance change has occurred at conductive pad 904. UID processor 520 can generate a clutch signal in response to detecting the change in capacitance of conductive pad 904. The clutch signal may be generated in response to the capacitive reading on conductive pad 904 surpassing a predetermined threshold.

Conductive pad 904 may be located between an outer surface of tracking sensor 214 and an interior surface of clutch cover 902. By contrast, clutch cover 902 may include an outer touch surface facing outward toward a surrounding environment. When a finger of user 107 touches the outer touch surface of clutch cover 902, the finger is separated from conductive pad 904 by a wall thickness of clutch cover 902. Clutch cover 902 can be formed from a dielectric material, e.g., a plastic, and thus, a capacitance across the wall of clutch cover 902 will change when the conductive finger of user 107 touches the outer touch surface. In another embodiment, clutch cover 902 can be made of a conductive material. A thickness of the wall may be limited to ensure that the change in capacitance is detectable. For example, the wall thickness of clutch cover 902 between the interior surface and the outer touch surface may be less than 1 mm. Accordingly, clutch cover 902 and conductive pad 904 provide a capacitive sensor on central axis 206 at device head 212.

Still referring to FIG. 9, finger clutch 802 can be located outside of a normal grasping area of UID 126. For example, finger clutch 802 can be distal to the exterior surfaces of grip cranks 216 that user holds during normal operation. Finger clutch 802 may, however, be within reach of a finger of user 107 when the user is manipulating UID 126. Accordingly, during normal operation, user 107 may extend the finger to touch finger clutch 802 and transmit a clutch signal to surgical robotic system 100.

Referring again to FIG. 8, additional touch sensitive areas and capacitive sensors may be used to command different functions of UID. In an embodiment, UID 126 includes at least one grip crank capacitive sensing pad 804 mounted on grip crank 216 of grip linkage 202. For example, grip crank capacitive sensing pad 804 may include an exterior surface of grip crank 216 between ridge 602 and a distal tip of grip crank 216. The touch sensitive area of the exterior surface may cover an underlying grip crank capacitive sensing pad 804 (FIG. 9). More particularly, a construction of grip crank capacitive sensing pad 804 may be similar to the construction of finger clutch 802 described above. Furthermore, like finger clutch 802, UID processor 520 may be electrically coupled to grip crank capacitive sensing pad 804 to detect a change in a capacitance of grip crank capacitive sensing pad 804. When UID processor 520 detects the capacitance above a predetermined threshold, UID processor 520 can generate a corresponding control signal. The corresponding control signal may be used to control one of several predetermined functions of surgical robotic system 100, as described below.

UID 126 is highly dexterous and finger-manipulated, and there is a chance that user 107 can drop UID 126 during a surgery. For safety reasons, an interlock may be used to prevent unintentional instrument movement when UID 126 is dropped. For example, a drop detection sensor can generate a drop signal in response to entering a free fall state when dropped. The drop detection sensor can be tracking sensor 214, which may monitor movement of UID 126. When tracking sensor 214 detects movement corresponding to a dropped state, the sensor generates an interlock off signal to pause or disconnect the interlock between UID 126 and surgical robotic system 100.

In an embodiment, the control signal generated by UID processor 520 in response to capacitance values of grip crank capacitive sensing pad 804 may be used to control the interlock between functions of UID 126 and surgical robotic system 100. More particularly, grip crank capacitive sensing pad 804 may be used to detect whether user 107 is holding UID 126 or whether UID 126 has been dropped. When user 107 is holding UID 126, movement of UID 126 may be interlocked to movement of surgical robotic system 100, e.g., movement of UID 126 detected by tracking sensor 214 may translate to corresponding movement of robotic arm 112. By contrast, when a drop state of UID 126 is detected, the interlock between UID 126 and surgical robotic system 100 movements may be paused or disconnected.

UID processor 520 can monitor the capacitance of grip crank capacitive sensing pad 804 to detect whether user 107 is holding UID 126. UID processor 520 can continuously monitor grip crank capacitive sensing pad 804 on a first grip crank 216 and one or more capacitive sensing pads on another grip crank 216. For example, UID processor 520 may monitor grip crank capacitive sensing pad 804 and a first capacitive sensing pad 806 on the second grip crank 216. In response to UID processor 520 detecting a capacitance of one or more of the capacitive sensing pads being below a predetermined threshold for a predetermined period of time, UID processor 520 can determine that UID 126 is in the drop state. For example, when the capacitance falls below the set threshold for at least five milliseconds, UID processor 520 can generate an interlock off signal. As used herein, the term "interlock off" can mean that teleoperation of a portion of surgical robotic system 100 is paused, e.g., in response to an unacceptable event or action. UID 126 can transmit the interlock off signal to surgical robotic system 100 to pause teleoperation of robotic arm 112 and/or surgical tool 104.

Still referring to FIG. 8, UID 126 may include at least one capacitive sensing pad on an exterior surface of each grip crank 216. At least one grip crank 216 may have several capacitive sensing pads on the exterior surface. For example, grip crank 216 may include first capacitive sensing pad 806, a second capacitive sensing pad 808, and/or a third capacitive sensing pad 810. The capacitive sensing pads may be mounted or arranged sequentially on the exterior surface of grip crank 216. For example, first capacitive sensing pad 806 may be distal to second capacitive sensing pad 808 on the exterior surface, and second capacitive sensing pad 808 may be distal to third capacitive sensing pad 810.

In an embodiment, the linear array of grip crank capacitive sensing pads 804 may be monitored by UID processor 520 to detect a swipe gesture. User 107 may input the swipe gesture by swiping a finger over the exterior surface of grip crank 216. The swipe can cause a sequence in changes in respective capacitances of first grip crank capacitive sensing pad 806, second grip crank capacitive sensing pad 808, and/or third grip crank capacitive sensing pad 810. UID processor 520 can detect the sequence of changes as a swipe gesture over the array of pads. The swipe gesture may be used to command various outputs. For example, the swipe gesture can trigger a control signal to cause robotic arm 112 to perform a predetermined operation. Alternatively, the swipe gesture can command some elements of a graphical user interface (GUI) of user console 120. For example, user 107 may swipe the exterior surface of grip crank 216 as a control input to navigate menus, scroll a displayed view, zoom in and out from a displayed image, or control other aspects of the GUI.

Capacitive sensing pads on some or all of the grip cranks 216 may be assigned to control an additional function. For example, a touch or swipe gesture detected by UID processor 520 can trigger a control signal to cause surgical tool 104 to deliver energy. More particularly, surgical tool 104 may be an energy instrument, e.g., a laser or an ultraviolet light source, and the predetermined touch entry may be detected to trigger activation of the energy instrument.

In an embodiment, grip cranks 216 used to command opening and closing of a surgical tool gripper can be alternated with grip cranks 216 used to command other functions such as GUI control or energy delivery control. By way of example, first set of grip linkages 404 can be used to command opening and closing of the surgical tool gripper. Furthermore, first set of grip linkages 404 may provide drop detection to detect the drop state of UID 126 and transmit the interlock off signal when UID 126 is not being held by user 107. By contrast, second set of grip linkages 406 may be used to command other functions of surgical robotic system 100. As described above, grip cranks 216 of the second set 406 may be positioned between adjacent grip cranks 216 of the first set 404. Accordingly, grip cranks 216 of first set 404 and second set 406 may be accessible in all rotational orientations of UID 126.

Tracking sensor 214 can be configured to generate a spatial state signal in response to movement of device body 204. The spatial state signal may correspond to a position and/or orientation of UID 126 in free space. The spatial state signal can control a motion of surgical robotic system 100, such as robotic arm 112. For example, when user 107 moves UID 126 rightward within the workspace, an end effector of robotic arm 112 may be controlled to move rightward also. Similarly, rotating UID 126 about central axis 206 may manipulate the end effector to similarly rotate in space about a corresponding longitudinal axis.

Tracking sensor 214 may include an accelerometer, a gyroscope, a magnetometer, or one or more other transducers capable of converting physical movement into a corresponding electrical signal. For example, tracking sensor 214 may include a magnetic tracking probe capable of measuring six degrees of freedom, including physical displacement (e.g., translation in XYZ space or another suitable coordinate system), roll, pitch, and yaw of UID 126. In an embodiment, several tracking sensors 214 are used to provide redundancy in position and/or orientation detection of UID 126. The tracking sensor(s) 214 can output electrical signal(s), and the electrical signal(s) can be combined, e.g., averaged, into the spatial state signal. The spatial state signal may be provided to control the motion of surgical robotic system 100.

Control signals input through UID 126 may be communicated to computer system 110 through a wired or wireless connection. In an embodiment, an electrical wire extends from a distal tip of UID 126, e.g., from distal end 210, to connect UID 126 to computer system 110. The electrical wire may provide power to UID 126 and may carry sensor signals, e.g., spatial state signals, grip signals, interlock off signals, clutch signals, etc., to computer system 110. Accordingly, UID 126 may be a peripheral device used to input commands to computer system 110. UID(s) 200 can be used in combination with other peripheral input devices. For example, a foot pedal switch may be connected to computer system 110 to provide a clutch input to surgical robotic system 100. Whereas each UID 126 may be individually clutched to pause teleoperation of respective robotic arms 112 or graspers of respective surgical tools 104, the respective robotic arms 112 or surgical tools 104 may be clutched at a same time by pressing the foot pedal switch. Thus, movement of actuators 114 may be manipulated by UIDs and other peripheral input devices of computer system 110.

Figure 10:
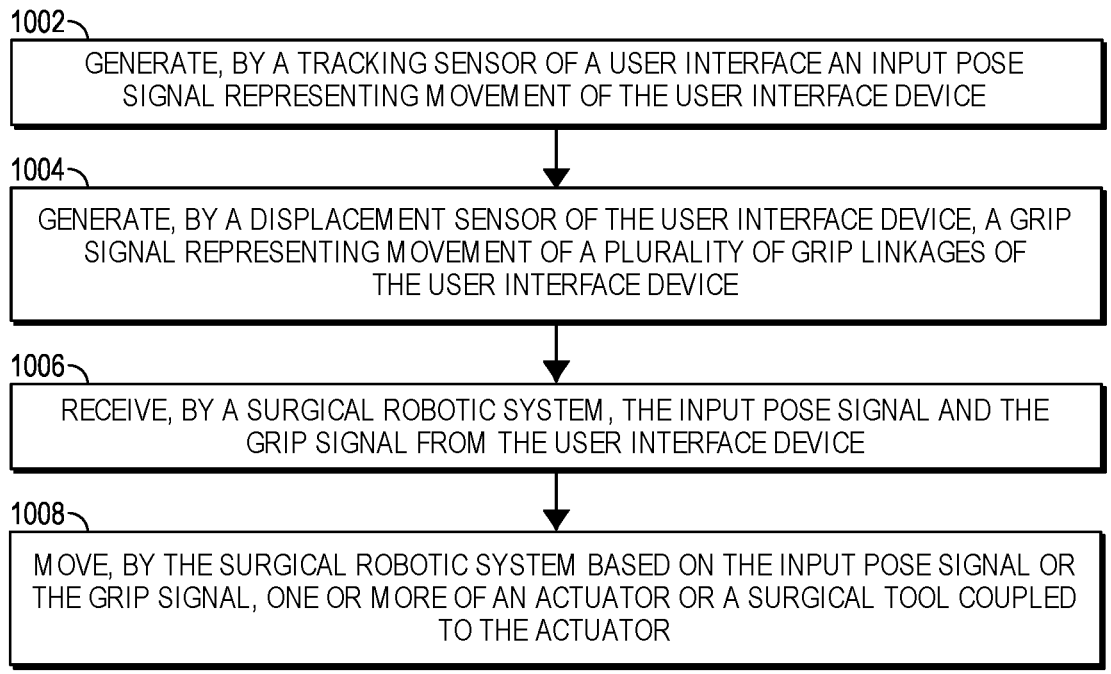
FIG. 10 is a flowchart of a method of controlling a surgical robotic system using a user interface device, in accordance with an embodiment.

Referring to FIG. 10, a flowchart of a method of controlling a robotic system using a user interface device is shown in accordance with an embodiment. The illustrated method corresponds to user 107 manipulating UID 126 to effect a movement of robotic arm 112 and/or surgical tool 104. For example, the illustrated method may correspond to user 107 commanding a grasper of surgical tool 104 to grasp tissue of patient 102.

The method for manipulating the robotic surgical tool in a surgical robotic system using a user interface device can include tracking movement of the user interface device in a space of six degrees of freedom. At operation 1002, tracking sensor 214 of UID 126 generates a spatial state signal, e.g., an input pose signal, representing movement of UID 126. The spatial state signal can be output to UID processor 520. UID processor 520 receives the spatial state signal from tracking sensor 214. UID processor 520 can analyze or modify the signal, and output the resulting spatial state signal to user console 120. User console 120 may in turn transmit the spatial state signal to surgical robotic system 100.

In addition to tracking movement of the UID in space, movement of one or more grip linkages of the UID can be detected. At operation 1004, grip linkage displacement sensor 518 of UID 126 generates a grip signal for controlling a grip motion of the surgical tool. The grip signal can represent movement of grip linkages 202 of UID 126. Grip linkage displacement sensor 518 can detect motion or position of slider 220 relative to a reference point of device body 204, e.g., a proximal surface of device head 212. The detected position information can be output to UID processor 520. UID processor 520 can detect, based on the received signal from grip linkage displacement sensor 518, a movement of grip linkages 202 relative to device body 204 of UID 126. UID 126 can analyze or modify the signal, to generate and output the resulting grip signal to user console 120. User console 120 may in turn transmit the grip signal to surgical robotic system 100.

At operation 1006, one or more processors of surgical robotic system 100 receives one or more of the spatial state signal, e.g., the input pose signal, or the grip signal from UID 126 via computer system 110. The control signals can be received via a wired or wireless connection to computer system 110. The control signals can be input to onboard processors associated with actuators 114 of robotic arms 112 and/or surgical tools 104. Accordingly, the spatial state signal and the grip signal can be processed to cause a movement of robotic arm 112 and surgical tool 104, respectively.

At operation 1008, surgical robotic system 100 moves an actuator 114 or a surgical tool 104 coupled to the actuator 114 based on at least one of the spatial state signal or the grip signal. Actuator 114 of surgical robotic system 100 can be moved in response to the spatial state signal. For example, the spatial state signal may represent a left to right movement of UID 126 within the workspace. Actuator 114 may correspondingly move in a manner that translates an end effector of robotic arm 112 from left to right. Similarly, surgical tool 104 of surgical robotic system 100 can be moved in response to grip signal. For example, the grip signal may represent a radially inward movement of grip cranks 216 as user 107 squeezes grip linkages 202. An actuator manipulating a grasper of surgical tool 104 may correspondingly move in a manner that moves jaws of the grasper radially inward in a pinching motion. Accordingly, robotic arm 112 and surgical tool 104 can be teleoperated based on manipulations of UID 126 to cause a grasper of surgical tool to grasp tissue of patient 102.

Figure 11:
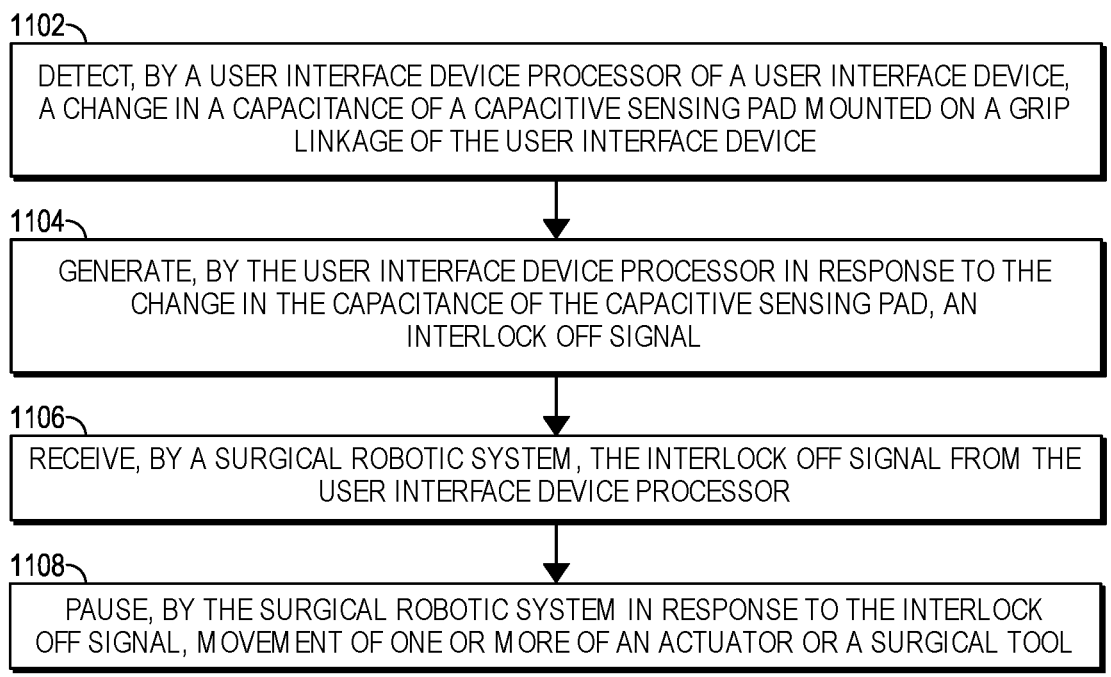
FIG. 11 is a flowchart of a method of controlling a surgical robotic system using a user interface device, in accordance with an embodiment.

Referring to FIG. 11, a flowchart of a method of controlling a robotic system using a user interface device is shown in accordance with an embodiment. The illustrated method corresponds to activation of a safety interlock to prevent unwanted movement of surgical robotic system 100 when user 107 drops UID 126.

At operation 1102, UID processor 520 detects a change in a capacitance of grip crank capacitive sensing pad 804 mounted on grip linkage 202 of UID 126. Grip crank capacitive sensing pad 804 may be located on an exterior surface of grip crank 216 distal to ridge 602. For example, a finger of user 107 may lose contact with grip crank capacitive sensing pad 804 when user 107 drops UID 126, and the loss of contact can change a detected capacitance of grip crank capacitive sensing pad 804.

At operation 1104, UID processor 520 can generate an interlock off signal in response to detecting the change in capacitance of grip crank capacitive sensing pad 804. UID processor 520 can determine, based on the detected change in capacitance, that UID 126 is in a drop state. That is, UID processor 520 can determine that UID 126 has been dropped or is no longer being held by user 107. In response to determining the drop state, UID processor 520 can generate the interlock off signal. UID processor 520 may transmit the interlock off signal to computer system 110 of user console 120. User console 120 may in turn transmit the interlock off signal to surgical robotic system 100.

At operation 1106, the interlock off signal is received by surgical robotic system 100 from UID processor 520. The interlock off signal can be received via a wired or wireless connection to computer system 110. The interlock off signal can be input to onboard processors associated with actuators of robotic arms 112 and/or surgical tools 104.

At operation 1108, surgical robotic system 100 pauses movement of an actuator 114 or a surgical tool 104 coupled to the actuator 114 in response to the interlock off signal. Movement of surgical robotic system 100 can be paused regardless of the spatial state signal. More particularly, as UID 126 falls to the ground it experiences rotational and translational movement that is represented in the spatial state signal generated by UID tracking sensor 214. Surgical robotic system 100 can receive the spatial state signal and ignore the spatial state signal when the interlock off signal is asserted. Similarly, movement of surgical robotic system 100 can be paused regardless of the grip signal. More particularly, when UID 126 hits the ground, grip cranks 216 may be forced radially inward by the impact. Surgical robotic system 100 can receive the grip signal and ignore the grip signal when the interlock off signal is asserted. Accordingly, unwanted or potentially harmful movement of surgical robotic system 100 can be prevented by the interlock off signal when UID 126 is dropped by user 107.

Figure 12:
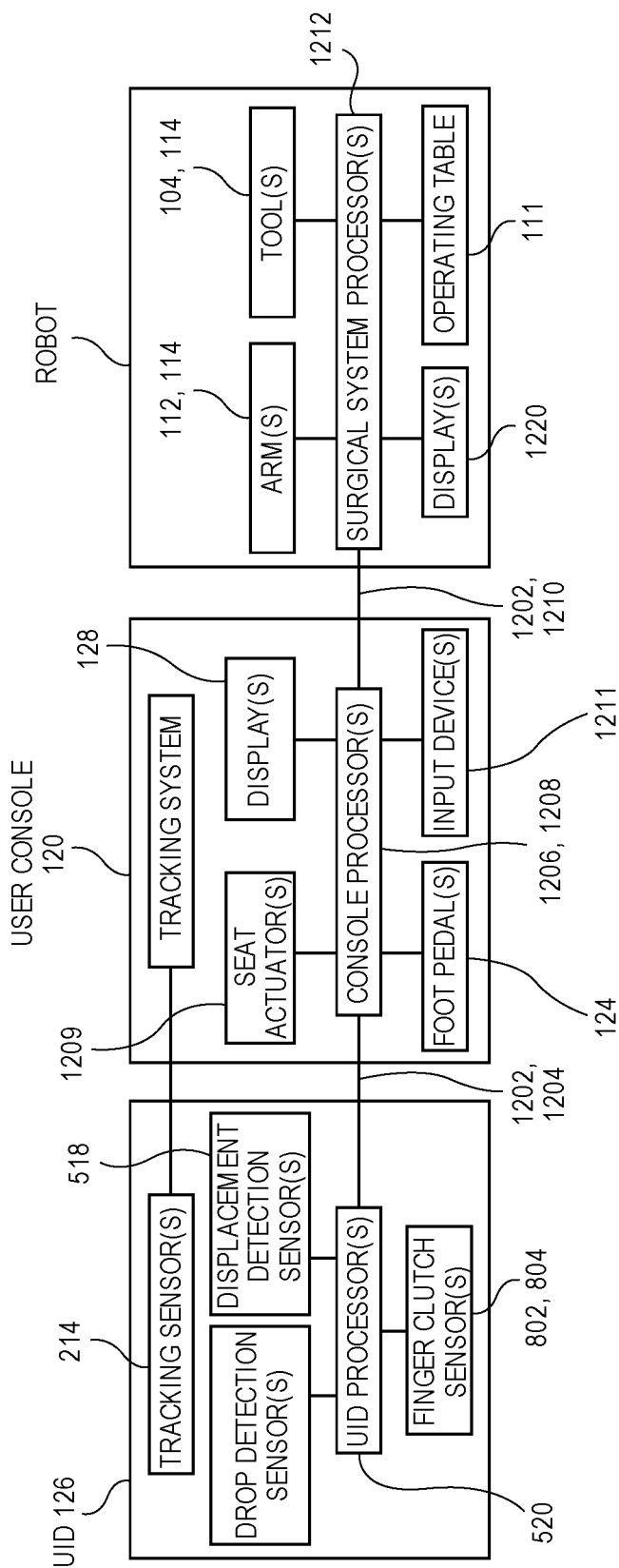
FIG. 12 is a block diagram of a computer portion of a surgical robotic system, in accordance with an embodiment.

Referring to FIG. 12, a block diagram of a computer portion of a surgical robotic system is shown in accordance with an embodiment. The surgical robotic system can include user console 120 having computer system 110 and one or more UIDs 126. Computer system 110 and UID 126 have circuitry suited to specific functionality, and thus, the diagrammed circuitry is provided by way of example and not limitation.

User console 120 can control portions of surgical robotic system 100, e.g., robotic arms 112 and/or surgical tools 104. UID 126 may be communicatively coupled to computer system 110 and/or surgical robotic system 100 to provide input commands to control surgical robotic system 100. For example, UID 126 may communicate electrical control signals 1202 to computer system 110, e.g., spatial state signals generated by UID processor 520 in response to signals from tracking sensor 214, grip signals generated by UID processor 520 in response to signals from grip linkage displacement sensor 518, clutch signals generated by UID processor 520 in response to detected changes in capacitance of conductive pad 904 of finger clutch 802, and interlock off signals generated by UID processor 520 in response to detected changes in capacitance of grip crank capacitive sensing pads 804, 806, 808, or 810. The electrical signals may be input commands to cause motion of surgical robotic system 100, or to pause motion of surgical robotic system 100.

The input electrical signals may be transmitted by UID processor 520 to a console processor 1206 of computer system 110 via a wired or wireless connection. For example, UID 126 may transmit the control signals 1202 to console processor 1206 via electrical wire 1204. Alternatively, UID 126 may transmit control signals 1202 to console processor 1206 via a wireless communication link. The wireless communication link may be established by respective RF circuitry of computer system 110 and UID 126. The wireless communication can be via radiofrequency signals, e.g., Wi-Fi or short range signals and/or suitable wireless communication protocols such as Bluetooth.

Console processor 1206 of computer system 110 may execute instructions to carry out the different functions and capabilities described above. Instructions executed by console processor(s) 1206 of user console 120 may be retrieved from a local memory 1208, which may include a non-transitory machine-readable medium. The instructions may be in the form of an operating system program having device drivers to control components of surgical robotic system 100, e.g., actuators 114 operatively coupled to robotic arm(s) 112 or surgical tool(s) 104.

In an embodiment, console processor 1206 controls components of user console 120. For example, one or more seat actuators 1209 can receive commands from console processor 1206 to control movement of seat 122. Seat actuator(s) 1209 can move seat 122 in one or more degrees of freedom, such as forward/backward, backrest tilt, headrest position, etc. Console processor 1206 can also transmit video data for presentation on display 128. Accordingly, console processor 1206 can control operation of user console 120. Input commands to seat actuator(s) 1209 or console processor 1206 can be entered by the user via foot pedal(s) 124 or another interface device 1211 such as a keyboard or a joystick.

Console processor 1206 can output control signals 1202 to surgical robotic system 100 via a link 1210. Control signals 1202 may be transmitted to control movement of surgical robotic system 100. Computer system 110 may be communicatively coupled to surgical robotic system 100 via wired or wireless links to output control signals 1202 to one or more surgical robotic system processor(s) 1212. For example, at least one processor 1212 can be located in control tower 130, and may be communicatively coupled to system components, such as surgical robotic platform 111 or one or more displays 1220. Actuators 114 of surgical robotic system 100 may receive control commands from surgical system processor 1212 to cause motion corresponding to movement of UID 126 or to pause motion of surgical robotic system 100 by clutching and/or disconnecting an interlock of surgical robotic system 100 when user 107 touches finger clutch 802 or drops UID 126.

Figure 13:
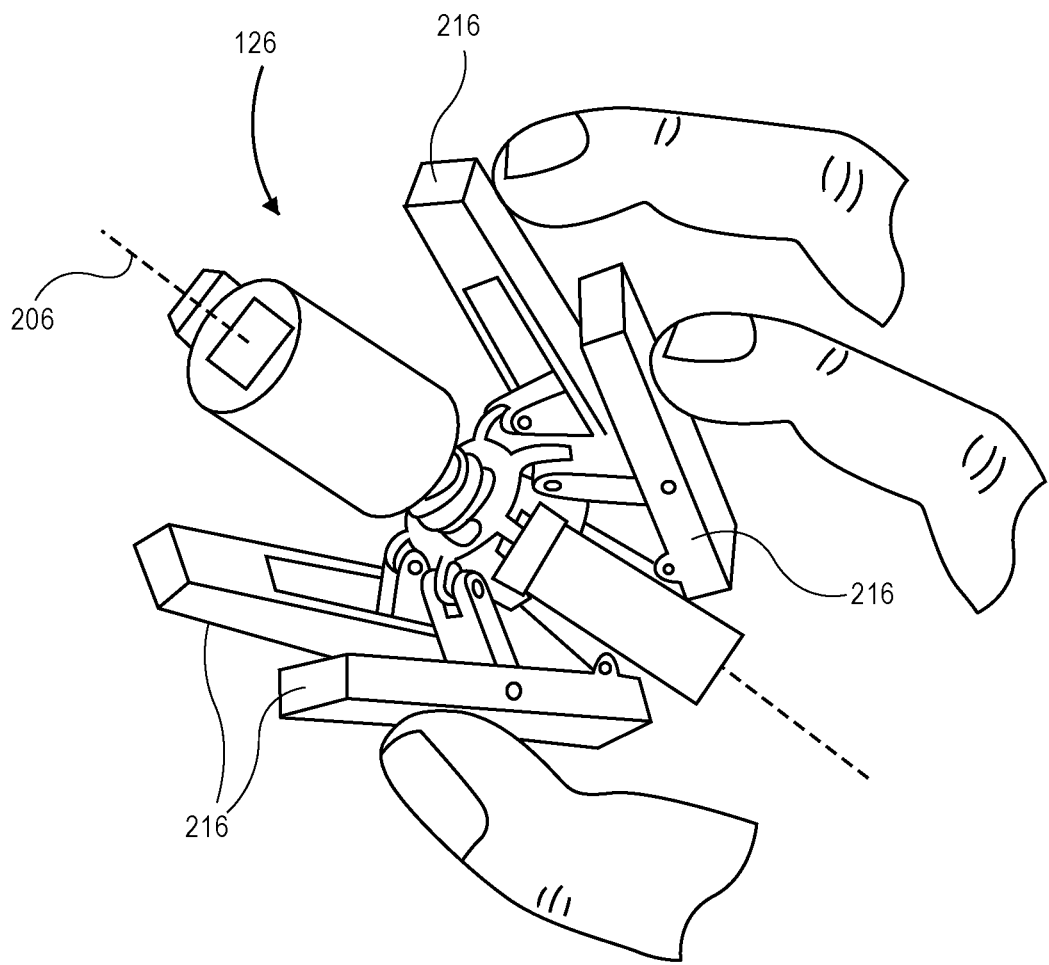
FIG. 13 is a perspective view of a user interface device being hand held in an open configuration, in accordance with an embodiment.

Referring to FIG. 13, a perspective view of a user interface device being hand held in an open configuration is shown in accordance with an embodiment. UID 126 is being held in a user's hand with grip cranks 216 in a fully open position. UID 126 allows for precise finger manipulation by the user. That is, the user's hand can rotate, roll, or twist the control grip. Furthermore, the grip cranks 216 can provide tactile feedback to the surgeon when the user's hand pinches or squeezes the grip cranks 216 inward toward axis 206. Accordingly, UID 126 provides enhanced dexterity and precision of movement.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A user interface device for manipulating a robotic surgical tool in a surgical robotic system, comprising:
    a device body having a central axis;
    a plurality of grip linkages distributed about the central axis, wherein each grip linkage is coupled to the device body by a slider at a prismatic joint; and
    a grip linkage displacement sensor configured to determine an axial position of the slider along the device body based on energy reflected from the slider and generate, based on the axial position of the slider, a grip signal for controlling a grip motion of the robotic surgical tool.

2. The user interface device of claim 1, wherein each grip linkage includes a grip crank coupled to the slider such that squeezing the grip cranks causes the slider to move along the central axis.

3. The user interface device of claim 2, wherein each grip crank is coupled to the slider by a follower arm coupled to the grip crank between a proximal end and a distal end of the grip crank.

4. The user interface device of claim 1, wherein, in a closed configuration, exterior surfaces of the plurality of grip linkages combine to provide a surface of revolution about the central axis.

5. The user interface device of claim 1, wherein each grip linkage includes a grip crank pivotally coupled to the device body at a device-crank joint.

6. The user interface device of claim 5, wherein the grip cranks extend from the device body along respective planes intersecting along the central axis, and wherein the respective planes are equiangular about the central axis.

7. The user interface device of claim 1, wherein the grip linkage displacement sensor includes a displacement detection sensor configured to emit energy toward a surface of the slider to detect movement of the slider over the device body.

8. A surgical robotic system, comprising:
    a robotic surgical tool mounted on a robotic arm;
    one or more user interface devices, wherein each user interface device includes
        a device body having a central axis,
        a plurality of grip linkages distributed about the central axis, wherein each grip linkage is coupled to the device body by a slider at a prismatic joint, and
        a grip linkage displacement sensor configured to determine an axial position of the slider along the device body based on energy reflected from the slider and generate, based on the axial position of the slider, a grip signal for controlling a grip motion of the robotic surgical tool; and one or more processors communicatively coupled to the one or more user interface devices and the robotic arm and configured to control the grip motion of the robotic surgical tool based on the grip signal.

9. The surgical robotic system of claim 8, wherein each grip linkage includes a grip crank coupled to the slider such that squeezing the grip cranks causes the slider to move along the central axis.

10. The surgical robotic system of claim 9, wherein each grip crank is coupled to the slider by a follower arm coupled to the grip crank between a proximal end and a distal end of the grip crank.

11. The surgical robotic system of claim 8, wherein, in a closed configuration, exterior surfaces of the plurality of grip linkages combine to provide a surface of revolution about the central axis.

12. The surgical robotic system of claim 8, wherein each grip linkage includes a grip crank pivotally coupled to the device body at a device-crank joint.

13. The surgical robotic system of claim 12, wherein the grip cranks extend from the device body along respective planes intersecting along the central axis, and wherein the respective planes are equiangular about the central axis.

14. The surgical robotic system of claim 8, wherein the grip linkage displacement sensor includes a displacement detection sensor configured to detect movement of the slider over the device body.

15. The surgical robotic system of claim 8, wherein the one or more user interface devices is a plurality of user interface devices, and wherein each user interface device generates a respective grip signal to control a grip motion of a respective robotic surgical tool coupled to a respective actuator of the surgical robotic system.

16. A method, comprising:
generate, by a grip linkage displacement sensor of a user interface device, a grip signal representing movement of a plurality of grip linkages of the user interface device, wherein the plurality of grip linkages are distributed about a central axis of a device body, and wherein each grip linkage is coupled to the device body by a slider at a prismatic joint, and the grip signal is generated based on an axial position of the slider that is determined by the grip linkage displacement sensor;

receive, by a surgical robotic system, the grip signal from the user interface device; and control, by the surgical robotic system based on the grip signal, a grip motion of a grasper of a robotic surgical tool coupled to an actuator.

17. The method of claim 16, wherein each grip linkage includes a grip crank coupled to the slider such that squeezing the grip cranks causes the slider to move along the central axis.

18. The method of claim 17, wherein each grip crank is coupled to the slider by a follower arm coupled to the grip crank between a proximal end and a distal end of the grip crank.

19. The method of claim 16, wherein, in a closed configuration, exterior surfaces of the plurality of grip linkages combine to provide a surface of revolution about the central axis.

20. The method of claim 16, wherein the grip linkage displacement sensor includes a displacement detection sensor, and further comprising detecting, by the displacement detection sensor, movement of the slider over the device body.

* * * * *